United States Patent
Colquhoun et al.

(10) Patent No.: US 8,932,298 B2
(45) Date of Patent: Jan. 13, 2015

(54) GUIDE ASSEMBLY

(75) Inventors: Callum Colquhoun, Beigrave (AU); Mark Fulton, Leeds (GB); Mick Rock, Leeds (GB)

(73) Assignee: Depuy International Limited, Beeston (GB)

( * ) Notice: Subject to any disclaimer, the term of this patent is extended or adjusted under 35 U.S.C. 154(b) by 1600 days.

(21) Appl. No.: 11/778,991

(22) Filed: Jul. 17, 2007

(65) Prior Publication Data

US 2008/0051798 A1    Feb. 28, 2008

(30) Foreign Application Priority Data

Jul. 21, 2006 (GB) .................................. 0614468.7

(51) Int. Cl.
| | |
|---|---|
| A61B 17/56 | (2006.01) |
| A61B 17/17 | (2006.01) |
| A61B 17/15 | (2006.01) |
| A61B 17/02 | (2006.01) |
| A61B 19/00 | (2006.01) |

(52) U.S. Cl.
CPC ........... *A61B 17/1764* (2013.01); *A61B 17/155* (2013.01); *A61B 2017/0268* (2013.01); *A61B 2019/467* (2013.01)
USPC ............................... 606/87; 606/88; 606/102

(58) Field of Classification Search
USPC ............................................. 606/87, 88, 102
See application file for complete search history.

(56) References Cited

U.S. PATENT DOCUMENTS

| | | | | |
|---|---|---|---|---|
| 4,703,751 A | * | 11/1987 | Pohl ................................ | 606/62 |
| 4,841,975 A | | 6/1989 | Woolson | |
| 5,484,446 A | * | 1/1996 | Burke et al. ..................... | 606/87 |
| 5,658,293 A | * | 8/1997 | Vanlaningham ................ | 606/88 |
| 5,688,280 A | * | 11/1997 | Booth et al. ..................... | 606/88 |
| 6,258,096 B1 | | 7/2001 | Seki | |
| 7,156,853 B2 | | 1/2007 | Muratsu et al. | |
| 2003/0069591 A1 | * | 4/2003 | Carson et al. .................. | 606/130 |
| 2004/0122305 A1 | * | 6/2004 | Grimm et al. .................. | 600/407 |
| 2007/0073304 A1 | * | 3/2007 | Seo et al. ......................... | 606/86 |

FOREIGN PATENT DOCUMENTS

| | | | |
|---|---|---|---|
| WO | WO 87/02883 A1 | 5/1987 | |
| WO | WO 94/08528 A1 | 4/1994 | |

OTHER PUBLICATIONS

GB Search Report dated Nov. 15, 2006.
New Jersey LCS Total Knee System, Surgical Technique, Depuy, Inc., 0601-87-000 (Rev. 1), 1995 (61 pages).
LCS Total Knee System Performance in Motion, Surgical Procedure, Depuy, 0611-74, 1989 (36 pages).
New Jersey LCS Total Knee System With Porocoat, Surgical Procedure by Frederick F. Buechel, M.D., 0611-78 (Rev. 3), 1987.
New Jersey LCS Total Knee Instrumentation, 0611-52 (Rev. 2) 1988, 1987 (2 pages).

(Continued)

*Primary Examiner* — Christian Sevilla

(57) ABSTRACT

A method for locating the mechanical axis of a long bone involves generating an image of the long bone and determining the angle between the mechanical axis of the bone and a reference axis, which contains at least two reference points towards one end of the bone. A reference arm is positioned relative to the at least two predetermined reference points, and the mechanical axis is located relative to the reference arm with reference to the previously determined angle.

12 Claims, 3 Drawing Sheets

(56) References Cited

OTHER PUBLICATIONS

Primary Total Knee Arthroplasty, William L. Rohr, Jr., Chapter 58, Published in Operative Orthopaedics, vol. 1, Michael W. Chapman, M.D., Editor, 1988, p. 713-726 (16 pages).

Primary Total Knees Standard Principles and Techniques Published in Knee Arthroplasty, Paul A. Lotke, M.D, 1995, pp. 65-67 (5 pages).
Computer Assisted Total Knee-Endoprothesis Using Planning Specific Individual Templates, F. Portheine, Fromel, K. Radermacher, Helmholtz-Institute for Biomedical Engineering at the RWTH Aachen, 1999-2000 Research Report, p. 142.

* cited by examiner

GUIDE ASSEMBLY

BACKGROUND TO THE INVENTION

The present invention relates to a guide assembly, and in particular a guide assembly for locating the mechanical axis of a bone.

During surgery it is often necessary to locate the mechanical axis of a bone. For example, during knee surgery it is necessary to find the mechanical axis of the femur so that the femur can be appropriately resected in order to properly fit a femoral prosthesis. It is known to determine the angle between the anatomical and mechanical axes using pre-operative x-ray or other images. During the procedure, the anatomical axis can be determined using an intramedullary rod, which is located in the bone's intramedullary canal. The mechanical axis can then be determined with reference to the pre-operative image data and the intramedullary rod. A disadvantage of this technique is the requirement to locate an instrument in the intramedullary canal.

SUMMARY OF THE INVENTION

The present invention provides a technique for locating the mechanical axis of a bone with reference to predetermined reference points towards the end of the bone, and with reference to pre-operative image data in which the mechanical axis is located relative to those reference points.

According to a first aspect of the invention, there is provided a guide assembly for locating the mechanical axis of a long bone comprising: a reference arm for location in direct or indirect contact with predetermined reference points on the long bone towards one end thereof, a locator for the reference arm for retaining it in place relative to the reference points on the long bone; an axis indicator which can rotate relative to the reference arm, and which can extend from the reference arm to indicate the orientation of the mechanical axis of the long bone relative to the predetermined reference points; and a scale for indicating the angle between the reference arm and the axis indicator.

It is possible to determine, pre-operatively, the angle between the reference arm at its location when in direct or indirect contact with the predetermined reference points, and the mechanical axis of long the bone. For example, the angle can be determined using an image of the long bone. The guide assembly of the invention can then be used during surgery in order to determine the mechanical axis. The reference arm can be located in direct or indirect contact with the predetermined reference points and retained in place using the locator. The axis indicator can be rotated so that the angle between the axis indicator and the reference arm is the same as the angle between the reference arm and the mechanical axis of long the bone that was determined pre-operatively, at which point the axis indicator will indicate the orientation of the mechanical axis.

Accordingly, the mechanical axis of a bone can be determined accurately during surgery using the guide assembly of the present invention without the use of an intramedullary rod.

The reference points are points on the bone, which enable a reference axis to be located such that the angle between the reference axis and the mechanical axis can be determined. Preferably, the reference points lie on the reference axis. Preferably, the reference points are located so that they can be viewed when the bone is viewed in the anterior-posterior direction. Preferably, the reference points are the distal most points on the long bone. For instance, when the long bone is a femur, preferably the reference points are the distal most points on the condyles of the femur. Preferably, the axis indicator rotates about a point, which also lies in the reference axis.

Preferably, the reference arm is configured to extend from the anterior side of the bone towards the posterior side to contact reference points on the distal face of the bone. Such a reference arm can be easier to locate in contact with the predetermined reference points in contrast with reference arms configured to contact reference points not on the distal face of the bone. Preferably, the axis indicator rotates relative to the reference arm in the coronal plane.

Preferably, the reference arm has at least one contact formation for direct contact with the reference points. Preferably, the at least one contact formation is a planar face. When there at least two contact formations, preferably the at least two contact formations are co-planar faces.

Providing a planar face, or a plurality of co-planar faces, is advantageous. This is because the predetermined reference points can be the distal most points of the long bone. Accordingly, the reference arm can easily be located in contact with the predetermined reference points by simply urging the planar face against the condyles. This technique is particularly advantageous because it can still be used when the condyles are damaged or corroded.

Preferably, the axis indicator comprises an axis indicator arm that extends proximally relative to the long bone. Preferably, the axis indicator arm has at least one guide formation for guiding a bone tool into the long bone. This is advantageous because, once the mechanical axis has been found, the long bone can be operated on immediately without the need to remove the guide assembly, and/or to locate an additional guide component. The guide formation can be an opening in the axis indicator arm. The opening can be a bore for guiding a tool, which can cut a bore in the bone. The opening can be a slot that defines a plane on which bone tissue can be cut by a bone saw or burr tool. The opening can be an engagement formation for receiving a corresponding engagement formation on a tool. Accordingly, the tool can be fastened to the axis indicator arm via the engagement formations so that the tool is fixed relative to the axis indicator and hence also to the bone. The tool could be a guide tool, which has formations for guiding a bone tool, which can cut, or drill into a bone. Optionally the tool can be a bone tool, which can cut or drill into a bone.

Preferably, the axis indicator arm is provided as a separate piece to the reference arm and can be detachably fastened to the reference arm. This is advantageous because it allows the use of types of different axis indicator arms with the reference arm.

The axis indicator can be configured to rotate relative to the reference arm in predetermined discrete steps. Preferably, the axis indicator can rotate relative to the reference arm so that the axis indicator can be positioned at any angle relative to the reference arm.

The scale can be provided by way of an indexing mechanism so that the angle between the axis indicator and the reference arm can be determined by counting the number of indexed steps during rotation of the axis indicator. Preferably, the scale is a visual scale. Preferably, the scale comprises a plurality of markings, which can be used to determine the angle between the axis indicator and the reference arm.

Preferably, the guide assembly further comprises an angle indicator arm, which is fixed relative to the reference arm and can be used in conjunction with the scale to indicate the angle between the reference arm and the axis indicator. The scale can be provided on one of the axis indicator and the angle indicator arm and can indicate the angle between the axis indicator and the angle indicator arm. As the angle indicator arm is fixed relative to the reference arm, the angle between the axis indicator arm and the reference arm can be determined from the angle between the axis indicator and the angle indicator arm. Preferably, the scale is provided on the axis indicator arm.

The scale can be provided on both of the axis indicator and the angle indicator arm. This can be advantageous because it can provide a more accurate indication of the angle between the axis indicator and the angle indicator arm. For instance, when the scale is provided on both the axis indicator and the angle indicator arm, the scale can be a Vernier scale.

Preferably, the angle indicator arm is provided as a separate piece to the reference arm and can be detachably fastened to the reference arm. Preferably, the angle indicator arm and the axis indicator arm are provided as a single component, which can be detachably fastened to the reference arm.

Preferably, the guide assembly further comprises a locking mechanism for locking the axis indicator relative to the reference arm. This is advantageous because, once the mechanical axis has been found by rotating the axis indicator relative to the reference arm, the axis indicator can be locked into position so that the axis indicator does not need to be held by the surgeon in order for it to continue to indicate the axis. This is also particularly advantageous when the axis indicator has guide formations because the locking mechanism prevents the axis indicator from moving due forces caused by a tool being guided by the guide formations acting against the axis indicator.

Preferably, the locator comprises a locator arm connected to the reference arm. Preferably, the locator arm is configured to contact a second bone adjacent to the long bone, so that the guide assembly can be located between the long bone and the second bone, and so that the locator arm can cause the reference arm to be urged against the end of the long bone. Preferably, the locator further comprises an adjustment mechanism for controlling the force by which the reference arm is urged against the long bone.

Preferably, the adjustment mechanism comprises a first handle connected to the reference arm and a second handle connected to the locator arm. Preferably, the first and second handles can be manipulated so as to increase the distance between the reference arm and the locator arm.

Preferably, the adjustment mechanism comprises a lock mechanism, which enables the distance between the reference arm and the locator arm to be maintained against forces acting against the reference arm and the locator arm.

The guide assembly will generally be made from metallic based materials, which are conventionally used in the manufacture of surgical instruments. Certain stainless steels can be particularly preferred. However, it will be understood that at least one part of the assembly, for instance the reference arm, can be made from polymeric materials. Using polymeric materials can reduce the cost of manufacture of the assembly, especially because an assembly made from polymeric materials can easily be manufactured using a moulding process. Suitable polymeric materials include certain polycarbonates, polyester, polyamides, poly-ether-ether ketones (PEEKs), and polyaryl-ether ketones (PAEKs). Polymeric materials can be reinforced with particulate material, especially fibrous materials, to provide appropriate wear and reinforcement characteristics.

According to a second aspect of the invention there is provided a method for locating the mechanical axis of a long bone comprising:

(a) generating an image of the long bone;

(b) determining the angle between the mechanical axis of the bone and a reference axis, which contains at least two reference points towards one end of the bone;

(c) positioning a reference arm relative to the at least two predetermined reference points; and (d) locating the mechanical axis relative to the reference arm with reference to the angle that is determined in step (b).

The image can be generated using any suitable method. For instance, the step of generating the image can comprise taking an X-ray of the long bone. Optionally, the image can be generated using any of a CT scan, ultra sound, or a MRI scan.

Preferably, the reference arm has an axis indicator fastened to it so that it can pivot relative to the reference arm. Preferably, step (d) comprises pivoting an axis indicator relative to the reference arm until the angle between the axis indicator and the reference arm is the same as the angle calculated in step (b).

INTRODUCTION TO THE DRAWINGS

DETAILED DESCRIPTION OF THE INVENTION

In the described embodiment the guide assembly of the invention is used to determine the mechanical axis of a femur. Nevertheless, it will be understood that the guide assembly can be used to determine the mechanical axis of other types of bone, such as the humerus.

Figure 1:
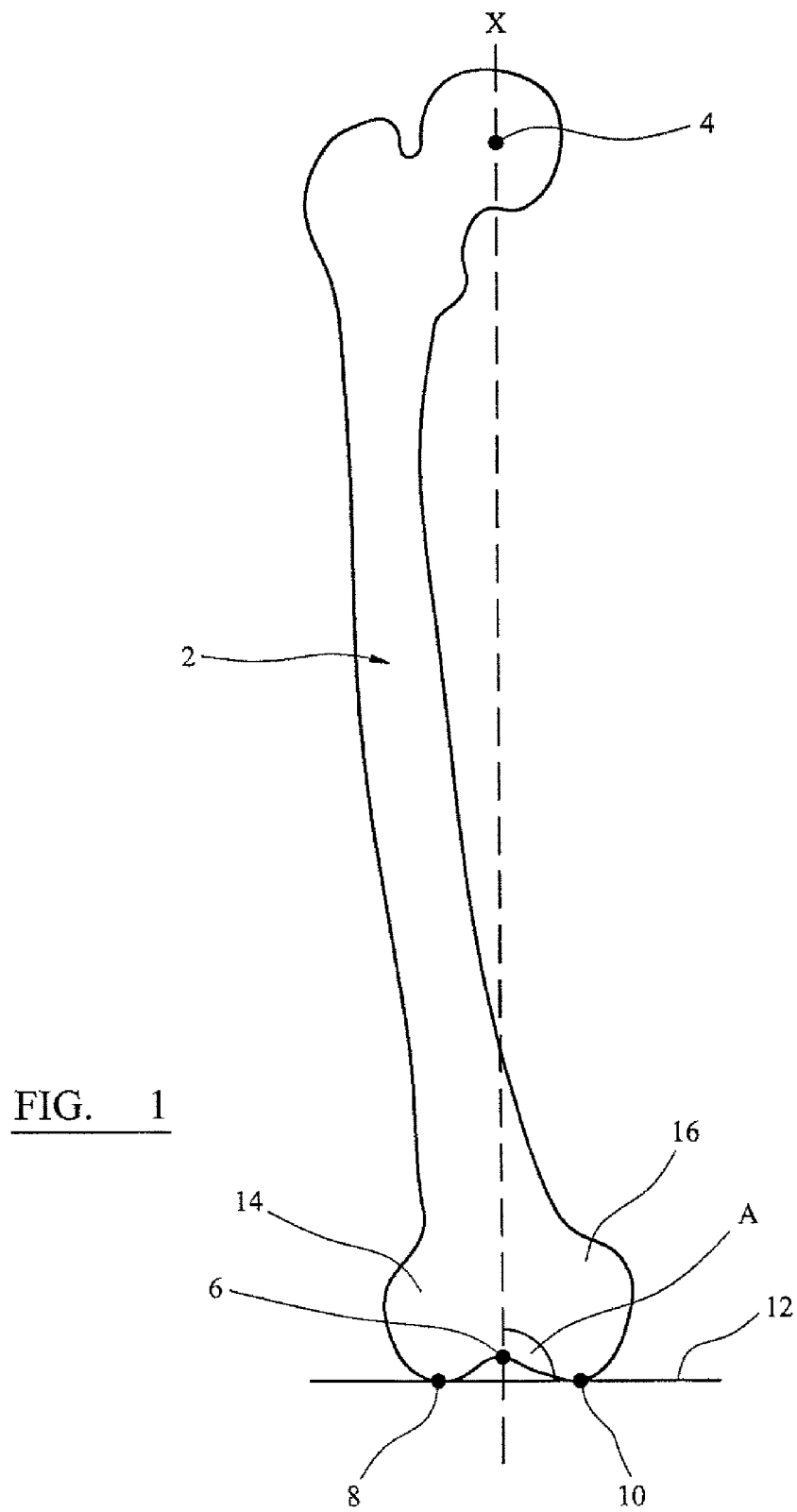
FIG. 1 is a side elevation view of a femur.

Referring to the drawings, FIG. 1 shows a femur 2 having a mechanical axis X. The mechanical axis X of the femur 2 is the line, which extends through the centre point 4 of the head of the femur and the centre point 6 of the intercondylar notch.

The angle A between the mechanical axis X and a reference axis 12 containing first 8 and second 10 reference points can be determined pre-operatively. In the described embodiment, the first 8 and second 10 reference points are the distal most points of the femurs first 14 and second 16 condyles. Nevertheless, as will be understood, this need not necessarily be the case and the reference points can be any other predetermined reference points on the femur 2. The angle A can be determined by obtaining an image of the femur 2 and then measuring on the image the angle between the mechanical axis X and the reference axis 12 containing the first 8 and second 10 reference points. The image of the femur 2 can be obtained by taking an X-ray of the femur 2.

Figure 2:
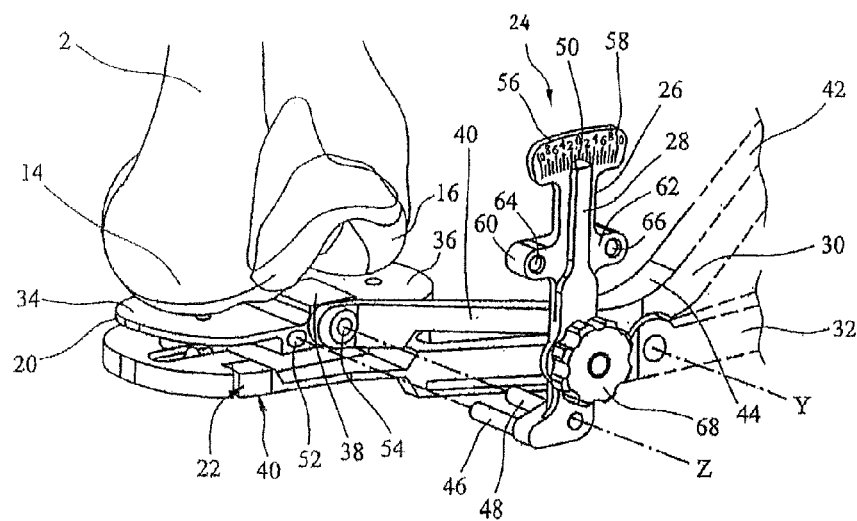
FIG. 2 shows a perspective view of a part assembled guide assembly according to the present invention, which can be used to indicate the mechanical axis of the femur shown in FIG. 1.
Figure 3:
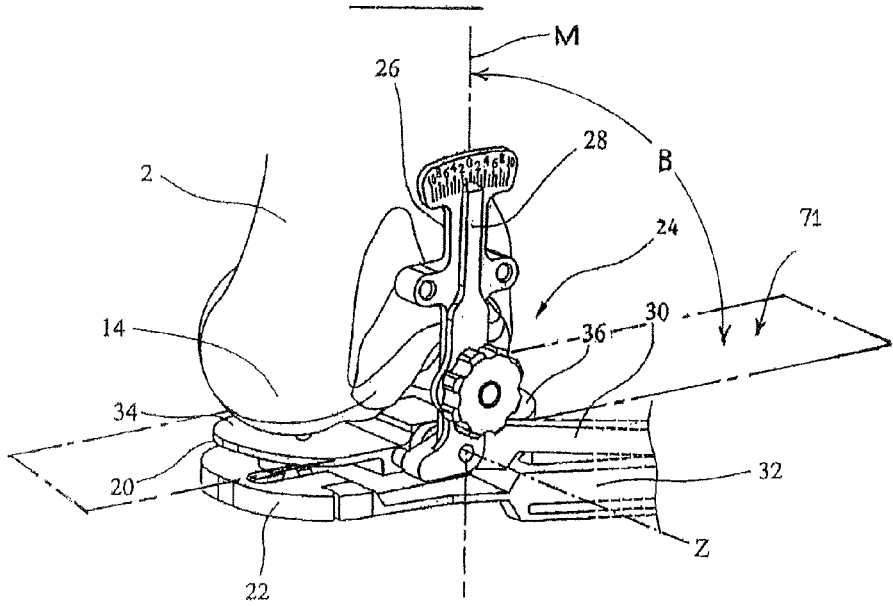
FIG. 3 shows a perspective view of the guide assembly shown in FIG. 2 fully assembled.

Referring to FIGS. 2 and 3, there is shown a guide assembly 20a according to the present invention located at the distal end of the femur 2. The guide assembly 20a is located between the femur 2 and the tibia, which is not shown for the sake of simplicity. The guide assembly 20a comprises a first plate 22 for abutment with the femur's condyles 14, 16, a second plate 24 for abutment with the proximal end of the tibia (not shown), an axis indicator arm 26, an angle indicator arm 28, and first 30 and second 32 handles connected to first 20 and second 22 plates respectively.

The first plate 20 has first 34 and second 36 planar faces separated by a bridge 38. The bridge provides strength to the first plate 20 as well as provides a housing for the opening 54 (discusses in more detail below). The first 34 and second 36 planar faces and the bridge 38 are shaped and sized so that the first 34 and second 36 planar faces can be brought into contact with the first 14 and second 16 condyles and so that the bridge 38 can sit in the intercondylar notch. The first 34 and second 36 planar faces are co-planar. The second plate 22 has a first face 40 for contact with the tibia.

The face of the first 20 plates which faces the face of the second 22 plates is configured so that the first 20 and second 22 plates can be brought together and fitted flush against each other.

The first handle 30 has first 40 and second 42 straight portions connected by a curved portion 44 toward the middle of the handle, such that the angle between straight lines extending along the length of the first 40 and second 42 straight portions is approximately 120°. The second handle 32 is substantially straight along its entire length.

The curved portion 44 of the first handle 30 is pivotally connected to the second handle 32 so that the first handle 30 can pivot relative to the second handle 32 about an axis Y which extends perpendicularly to the lengths of the first 30 and second 32 handles.

The first handle 30 is connected to the bridge 38 of the first plate 20 so that the first plate 20 can rotate relative to the first handle 30 about an axis Z that extends along the length of the bridge 38 and is contained within the planes of the first 34 and second 38 planar faces.

The second handle 32 is connected to second plate 22 so that they cannot move relative to each other. In the embodiment described, the second plate 22 and the second handle 32 are provided as a single moulded piece.

Figure 4:
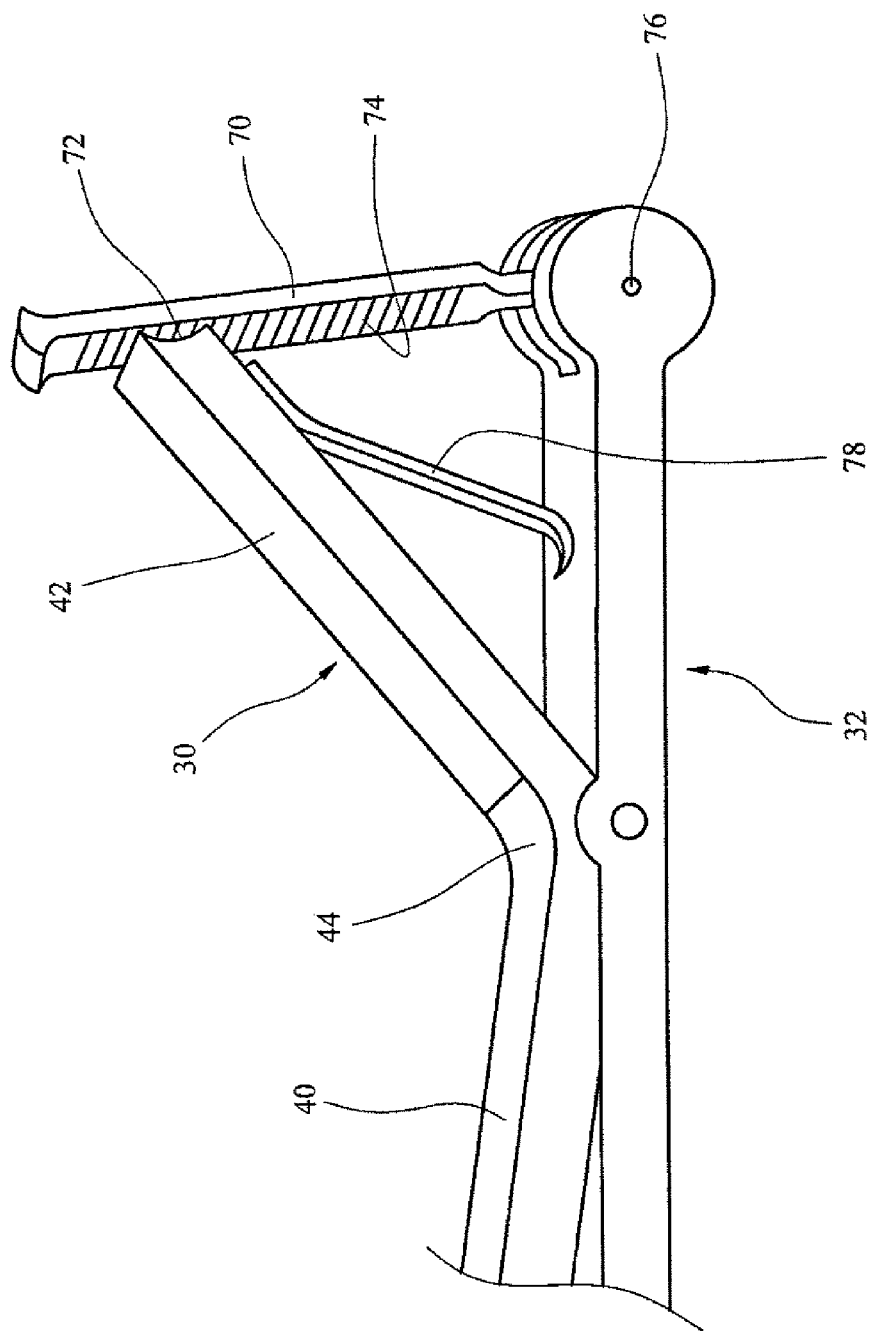
FIG. 4 shows a perspective view of the first and second handles of the guide assembly.

As shown in FIG. 4, a locking arm 70 is attached to the end of the second handle 32 that is distal to the second plate 22 by a pivot 76. The locking arm 70 has a plurality of teeth 74 arranged on a first face. The locking arm 70 can rotate relative to the second handle 32 about the pivot, so that the first face of the locking arm 70 can be brought into contact with the end of the first handle 30 that is distal to the first plate 20. Furthermore, the locking arm 70 is biased towards contact with the first handle 30. The end of the first handle 30 distal to the first plate 20 has a hook 72 which can engage the teeth 74. The teeth 74 and hook 72 are configured so that the hook 72 can easily slide over the teeth 74 when moved in a direction toward the second handle 32, but so that the hook 72 is prevented from sliding over the teeth in the opposite direction. A leaf spring 78 is attached to the first handle 30 towards its end distal to the first plate 20. The leaf spring 78 is biased the against the second handle 32 so that the ends of the first 30 and second 32 handles that are distal to the first 20 and second 22 plates are biased away from each other. Accordingly, the locking arm 70, hook 72 and leaf spring 78 arrangement provide a ratchet mechanism which enables distance between the first 20 and second 22 plates to easily be selected and locked as described in more detail below.

The angle indicator arm 28 is provided as a separate piece to the first plate 20. The angle indicator arm 28 has first 46 and second 48 pegs extending perpendicularly to its length at its first end. The second end of the angle indicator arm 28 narrows to a tip 50. The first peg 46 can be received in a first 52 bores in the first plate 20. The second peg 48 can extend through a first opening 54 in the end of the first straight portion 40 of the first handle 30, and be received in a second bore (not shown) in the first plate 20. When the first 46 and second 48 pegs are received in the first 52 and second bores of the first plate, the angle indicator arm 28 extends perpendicularly to the planes of the first 34 and second 36 planar faces.

A first end of the axis indicator arm 26 is connected to the first end of the angle indicator arm 28 so that when the guide assembly 24 is assembled, the axis indicator arm 26 can rotate relative to the angle indicator arm 28 and to the first plate about the axis Z. A scale 58 is provided on a head 56 at a second end of the axis indicator arm 26. The lengths of the axis indicator arm 26 and the angle indicator arm 28 are such that the tip 50 of the angle indicator arm is in the region of the scale 58 on the head 56. The axis indicator arm 26 also has first 60 and second 62 limbs extending substantially perpendicularly to the length of the axis indicator arm 26. The first limb 60 has a first opening 64 formed in it and the second limb 62 has a second opening 66 formed in it. The first 64 and second 66 openings define an axis along which a bone drill bit can be extended. The axes run substantially parallel to the axis Z. A straight line connecting the centre points of the first 64 and second 66 openings runs substantially perpendicular to the length of the axis indicator arm 26.

A wheel 68 is provided on the angle indicator arm 28. The wheel 68 has a threaded spigot (not shown), which extends through and engages a threaded hole (not shown) in the angle indicator arm 28. Rotating the wheel 68 clockwise causes the spigot to travel through the angle indicator arm 28 towards the axis indicator arm 26. The length of the spigot is such that the wheel 68 can be rotated so that the end of the spigot can be driven into and engages the axis indicator arm 26. Once engaged, the spigot prevents the axis indicator arm 26 rotating relative to the angle indicator arm 28. Rotating the wheel 68 anti-clockwise causes the spigot to travel out of the angle indicator arm 28 away from the axis indicator arm 26, thereby disengaging the spigot from the axis indicator arm 28.

In use, the angle between the reference axis 12 containing the first 8 and second 12 reference points and the mechanical axis X is calculated from an X-ray image of the femur 2. The first 20 and second 22 plates are then located between the distal end of the femur 2 and the proximal end of the tibia (not shown) so that the first 34 and second 36 planar faces of the first 20 plate face toward the first 14 and second 16 condyles.

The ends of the first 30 and second 32 handles that are distal to the first 20 and second 22 plates are then squeezed together. This causes the handles 30, 32 to rotate relative to each other about axis Y, so that the first 20 and second plates 22 are separated from each other. This causes the first 34 and second 36 planar faces of the first plate 20 to be urged against the first 14 and second 16 condyles of the femur 2, and the first face 40 of the second plate 22 to be urged against the tibia. This helps to prevent the first plate 20 from moving relative to the femur 2. As the first 34 and second 36 planar faces are co-planar, urging the first plate 20 against the first 14 and second 16 condyles will help ensure that the first 34 and second 36 planar faces contact the first 8 and second 10 reference points (which are the most distal points of the femur's condyles). Accordingly, the plane containing the first 34 and second 36 planar faces will also contain the first 8 and second 10 reference points.

The hook 72 and teeth 74 arrangement will ensure that the ends of the handles 30, 32 distal to the first 20 and second 22 plates do not separate under the force of the femur 2 and tibia on the first 20 and second 22 plates. If it is necessary to reduce the distance between the first 20 and second 22 plates, such as when the surgical procedure is complete, then the locking arm 70 can be rotated away from the first handle 30 so as to release the hook 72 from the teeth 74. The end of the first handle 30 that is distal to the first plate 20 will then be forced away from the second handle 32 due to the leaf spring 78, thereby causing the distance between the first 20 and second 22 plates to decrease.

The axis indicator arm 26 and the angle indicator arm 28 are then connected to the first plate 20 by way of receiving the first 46 and second 48 pegs within the first 52 and second bores in the first plate 20. When initially connected to the first plate 20, the axis indicator arm 26 and the angle indicator arm 28 extend perpendicularly to the plane of the first 34 and second 36 planar faces.

The axis indicator arm 26 is then rotated relative to the angle indicator arm 28 until the tip 50 of the angle indicator arm 28 points towards the angle which is equal to 90° minus the angle between the reference axis 12 containing the first 8 and second 12 reference points and the mechanical axis X. The angle between the plane 71 of the planar face 34 of the first plate 20 and an axis M through the axis indicator arm 26 is shown in FIG. 3 as β. Once this position has been reached, the length of the axis indicator arm 26 extends along the length of the mechanical axis X. Accordingly, the mechanical axis X has been found and the first 64 and second 66 openings can be used to guide a drill bit into the femur 2 to prepare bores in femur 2 for receiving corresponding pins of a cutting guide or a cutting tool (not shown). Optionally, the first 64 and second 66 openings can be used to mount a cutting guide directly on the axis indicator arm 26. The cutting guide can then be used to guide a cutting tool into the femur 2.

What is claimed is:

1. A method for locating during a surgical procedure a mechanical axis of an uncut bone having an end with an external surface, comprising the steps of:
    (a) generating an image of the uncut bone including the external surface;
    (b) defining the mechanical axis of the uncut bone on the image of the uncut bone;
    (c) measuring an angle between the mechanical axis of the uncut bone as defined in step (b) and a reference axis on the image of the uncut bone, the reference axis containing at least two reference points located on the image of the external surface of the uncut bone;
    (d) during surgery, contacting at least two points on the external surface of the uncut bone with a first plate, the first plate being fastened to an angle indicator, the angle indicator being pivotably fastened to an axis indicator, at least one of the axis indicator and the angle indicator including a scale to indicate an angle between the angle indicator and the axis indicator; and
    (e) positioning the axis indicator relative to the angle indicator such that the angle indicated on the scale has a predetermined relationship with the angle measured in step (c).

2. The method of claim 1, wherein step (e) comprises the step of pivoting the axis indicator relative to the first plate until the angle between the axis indicator and the first plate is substantially the same as the angle measured in step (c).

3. The method of claim 1, wherein the uncut bone is a femur.

4. The method of claim 3, wherein the end of the uncut bone includes a medial condyle and a lateral condyle, and one of the at least two reference points is on the medial condyle and one of the at least two reference points is on the lateral condyle.

5. The method of claim 3, wherein the femur includes a medial condyle and a lateral condyle, the medial condyle has a medial distal facing surface and the lateral condyle has has a lateral distal facing surface, and one of the at least two reference points is on the image of the medial distal facing surface and one of the at least two reference points is on the image of the lateral distal facing surface.

6. The method of claim 3, further comprising the steps of:
    handling a guide assembly comprising the first plate, the angle indicator, the axis indicator and a second plate.

7. The method of claim 1, wherein the axis indicator has an arm with at least one bore formed therein for guiding a tool that can form a bore in the uncut bone.

8. The method of claim 1, wherein the axis indicator comprises an axis indicator arm that is detachably fastened to the first plate, and further comprising the step of attaching the axis indicator arm to the first plate.

9. The method of claim 1, further comprising a locking mechanism for locking the axis indicator against rotation relative to the first plate.

10. The method of claim 1, wherein the axis indicator rotates about a point that lies on the reference axis.

11. The method of claim 6, wherein the second plate is pivotably connected to the first plate and is configured to contact a second bone adjacent to the uncut bone such that the guide assembly can be located between the uncut bone and the second bone, and so that the second plate can cause the first plate to be urged against the end of the uncut bone.

12. A method for locating during a surgical procedure a mechanical axis of an uncut bone having an end with an external surface, comprising the steps of:
    (a) generating an image of the uncut bone including the external surface;
    (b) defining the mechanical axis of the uncut bone on the image of the uncut bone;
    (c) measuring an angle between the mechanical axis of the uncut bone as defined in step (b) and a reference axis on the image of the uncut bone, the reference axis containing at least two reference points located on the image of the external surface of the uncut bone;
    (d) during surgery, positioning a planar surface of a first plate relative to at least two points on the external surface of the uncut bone, the two points on the external surface of the uncut bone corresponding with the two reference points on the image of the uncut bone, the first plate being fastened to an angle indicator, the angle indicator being pivotably fastened to an axis indicator; and
    (e) positioning the axis indicator relative to the first plate on the uncut bone such that the angle between the axis indicator and the planar surface of the first plate is substantially the same as the angle measured in step (c).

* * * * *